(12) United States Patent
Osa et al.

(10) Patent No.: US 8,774,891 B1
(45) Date of Patent: Jul. 8, 2014

(54) CORTICAL ELECTRODE ASSEMBLIES

(75) Inventors: Benjamin Osa, Chanhassen, MN (US); Eric Caillé, Chanhassen, MN (US)

(73) Assignee: PMT Corporation, Chanhassen, MN (US)

( * ) Notice: Subject to any disclaimer, the term of this patent is extended or adjusted under 35 U.S.C. 154(b) by 193 days.

(21) Appl. No.: 12/927,461

(22) Filed: Nov. 16, 2010

Related U.S. Application Data (60) Provisional application No. 61/281,327, filed on Nov. 16, 2009.

(51) Int. Cl.
*A61B 5/04* (2006.01)
*A61N 1/00* (2006.01)

(52) U.S. Cl.
USPC ............................ 600/378; 600/544; 607/118

(58) Field of Classification Search
CPC . A61N 1/0551; A61N 1/0539; A61N 1/0529; A61N 1/0534; A61N 1/0565; A61N 1/0558; A61B 5/0478

USPC ......... 600/372–374, 377–378, 393, 544–545; 607/115–118

See application file for complete search history.

(56) References Cited

U.S. PATENT DOCUMENTS

| | | | | |
|---|---|---|---|---|
| 4,461,304 | A | | 7/1984 | Kuperstein |
| 5,390,671 | A | * | 2/1995 | Lord et al. .................... 600/347 |
| 5,919,220 | A | * | 7/1999 | Stieglitz et al. ............... 607/118 |
| 7,006,859 | B1 | * | 2/2006 | Osorio et al. ................. 600/378 |
| 8,086,322 | B2 | * | 12/2011 | Schouenborg ................ 607/115 |
| 8,255,061 | B2 | * | 8/2012 | Perlin et al. .................... 607/116 |

* cited by examiner

*Primary Examiner* — Linda Dvorak
*Assistant Examiner* — Brian M Antiskay
(74) *Attorney, Agent, or Firm* — Eggink & Eggink; Anthony G. Eggink; Katrina M. Eggink (57) ABSTRACT

Cortical electrode assemblies having a first flexible electrode body and a second flexible electrode body. The first electrode body may have an array of macro electrode contacts and the second electrode body may have a micro-wire electrode array or a depth electrode structure. The first electrode body has at least one aperture and the second electrode body may have a grommet-like body structure which may be positioned in predetermined thru holes of the first electrode body with respect to the electrode grid.

20 Claims, 9 Drawing Sheets

CORTICAL ELECTRODE ASSEMBLIES

This Application claims the benefit of U.S. Provisional Patent Application Ser. No. 61/281,327, filed on Nov. 16, 2009.

BACKGROUND OF THE INVENTION

The present invention relates generally to cortical electrode assemblies for recording and stimulating. Particularly, this invention relates to cortical electrode structures adapted for use with micro-wire arrays and depth electrode structures. More particularly, the invention relates to cortical electrode assemblies and a process for forming electrode assemblies which are versatile and which may incorporate combinations of macro electrodes, micro-wire electrode arrays and depth electrodes.

Cortical and depth electrodes are used for monitoring recordable electrical brain activity or electroencephalograph (EEG) signals when less invasive methods do not provide the electrophysiology data necessary. The electrode recording is performed directly on the surgically exposed brain or inside the brain which may be necessary when the seizure focus is too small and/or too deep within the brain to produce a recordable EEG signal. The electrodes are also used for decoding EEG activity, and for stimulation.

The cortical electrode assemblies of the invention allow medical staff the versatility of joining various electrode devices into a cortical electrode assembly and which may include the use of macro electrode contacts, micro-wire contacts and depth electrodes.

Micro-wire electrodes are cortical electrodes having electrode contacts using the diameter of the wire structure itself as the electrode contact. The remainder of the wire electrode structure is insulated so that the only conductive portion of the micro-wire electrode is the exposed cross section of the wire end which is generally perpendicular to the length of the wire itself. Micro-wire electrodes do not utilize flat disc electrode contacts that a lead wire is crimped, welded or otherwise connected to, for example.

Micro-wires may be of different diameters, for example, ranging from 5 microns to several millimeters. The typical micro-wire diameter may range between 25 microns to 175 microns and may be configured in a grid array having the micro-wires differently spaced center to center from the electrode body. Micro-wire electrode devices have leads extending from the device and which may terminate into various interconnecting structures such as an inline tail, a PCB board, or bare wire leads.

This application provides related subject matter to that of utility patent application U.S. Ser. No. 12/924,657 ('657 Application), filed Oct. 1, 2010 and titled Improved Electrode for Recording and Stimulation and which is incorporated by reference herein. The '657 Application and this Application are assigned to and commonly owned by PMT Corporation.

SUMMARY OF THE INVENTION

The present invention relates to cortical electrode assemblies used for recording and stimulation. The electrode assemblies include improved electrode structures as well as methods of joining multiple electrode structures which enhance the use and effectiveness of cortical electrodes.

The present invention relates to a multiple part cortical medical electrode assembly which utilizes an electrode structure, such as a micro-wire array, in conjunction and in cooperation with a base cortical medical electrode. The invention provides for the flexibility in the positioning of the second electrode structure with respect to the electrode contact grid of the base cortical electrode, for example. A grommet-like attachment structure may be utilized for quickly and economically securing a second electrode structure into a thru-hole of the base cortical electrode structure. Keyed thru-hole configurations may also be utilized to further secure the second electrode structure to the base electrode structure. Other securement structures may also be utilized in the multiple part cortical medical electrode assemblies of the invention.

The invention further relates to improved electrode features, manufacturing methods and the use of cortical medical electrode devices. The micro-wire cortical electrode assemblies utilize a generally multiple part electrode structure, such as a two-part structure, to give a physician the flexibility and option to add micro-wire arrays or depth electrodes where deemed necessary. This option is provided by producing a standard cortical strip or grid electrode device with thru holes between the standard electrode contacts that allow for the addition of a micro-wire array(s) or a depth electrode, for example. The base cortical electrode device may have pre-perforated apertures which permit a plurality of desired locations for the second electrode device. Additionally, an electrode assembly structure may be provided comprising a platform with a thru-hole and a handheld introducing rod or guiding stylet which allows for easy assembly of the micro-wire array into the cortical strip electrode and in a sterile field.

These and other benefits and advantages of this invention will become clear from the following description by reference to the drawings.

DESCRIPTION OF THE PREFERRED EMBODIMENTS

Referring to FIGS. 1-6, a cortical strip or grid electrode structure 16 is shown having a base body structure 21 with electrode contacts 18 positioned in 2×4 grid contact pattern on one side of the base strip body 21. Any number of conductive electrode contacts 18 and electrode grid patterns of electrode contacts 18 may be utilized within the purview of the present invention. A pair of spaced apertures or thru-holes 17 are shown positioned within the grid of electrode contacts 18.

Figures 1, 2:
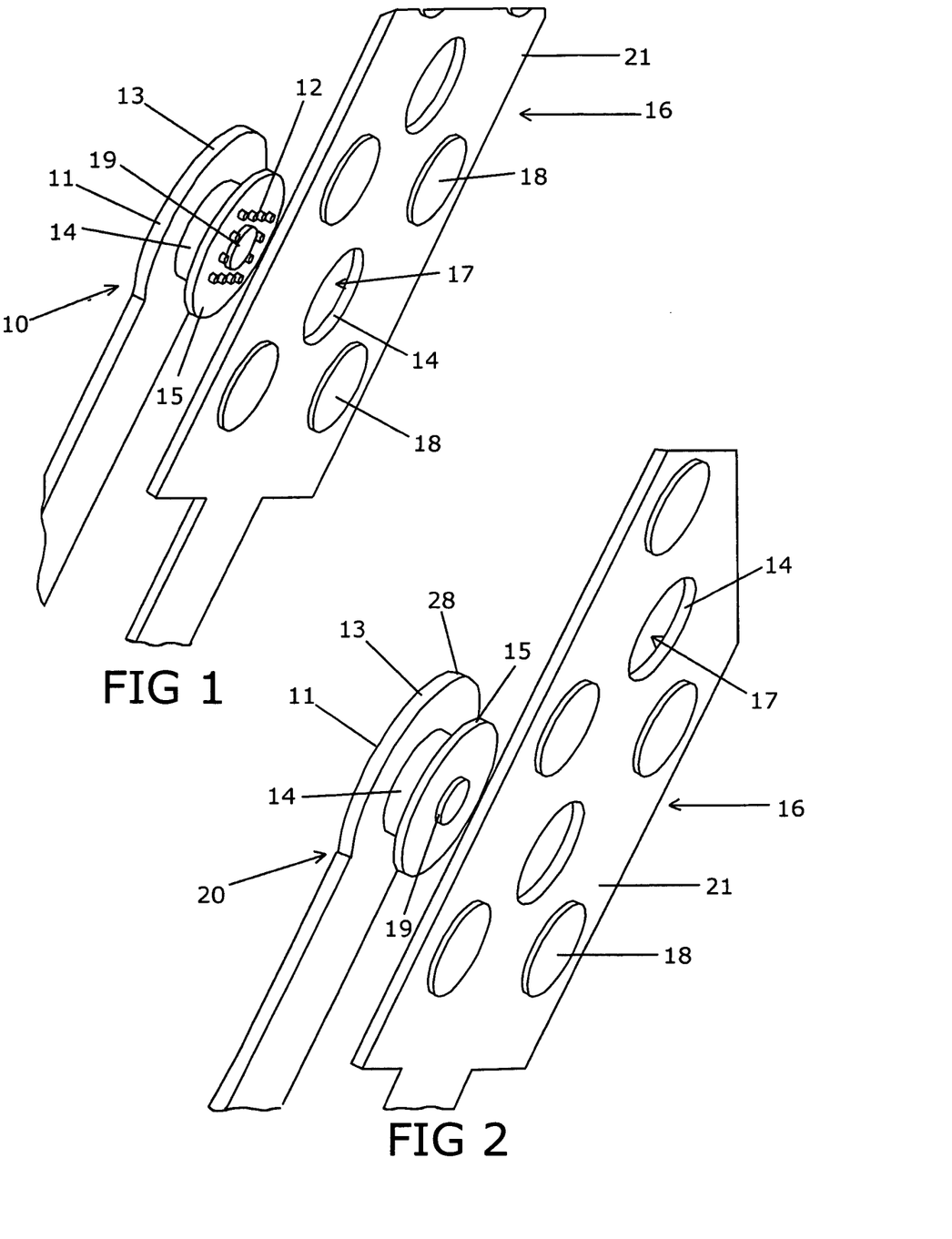
FIG. 1 is a perspective view showing the micro-wire electrode device of the invention positioned for placement in a thru hole of a cortical strip or grid electrode structure.
FIG. 2 is a perspective view showing another electrode structure positioned for placement in a thru hole of a cortical strip or grid electrode structure.

FIGS. 1-6 further show a plurality of second electrode structures, i.e., electrode structure 10 (FIG. 1), structure 20 (FIG. 2), structure 22 (FIG. 3), structure 24 (FIGS. 5 and 6), adapted to be positioned within selected thru-holes 17 of the base body structure 21 of electrode structure 16. In FIG. 1 the second electrode structure 10 is shown to have a body structure 11 which is constructed and arranged to be secured in a selected thru-hole 17 of the base body structure 21 of cortical electrode device 16. In FIG. 2, the second electrode structure is shown to have an elongated body having a rounded terminal end also positioned for securement in electrode structure 16. The body structures of the second electrodes 10 and 20 are formed of a medical grade silicone substrate, for example, each having a rounded end with a first diameter 13. Two circular body portions with diameters 14 and 15 are shown to extend outwardly from the body 11. The outward circular body portion having diameter 15 may have any desired second electrode contact(s) structure(s) comprising macro, micro or depth electrode structures, for example.

Figure 3:
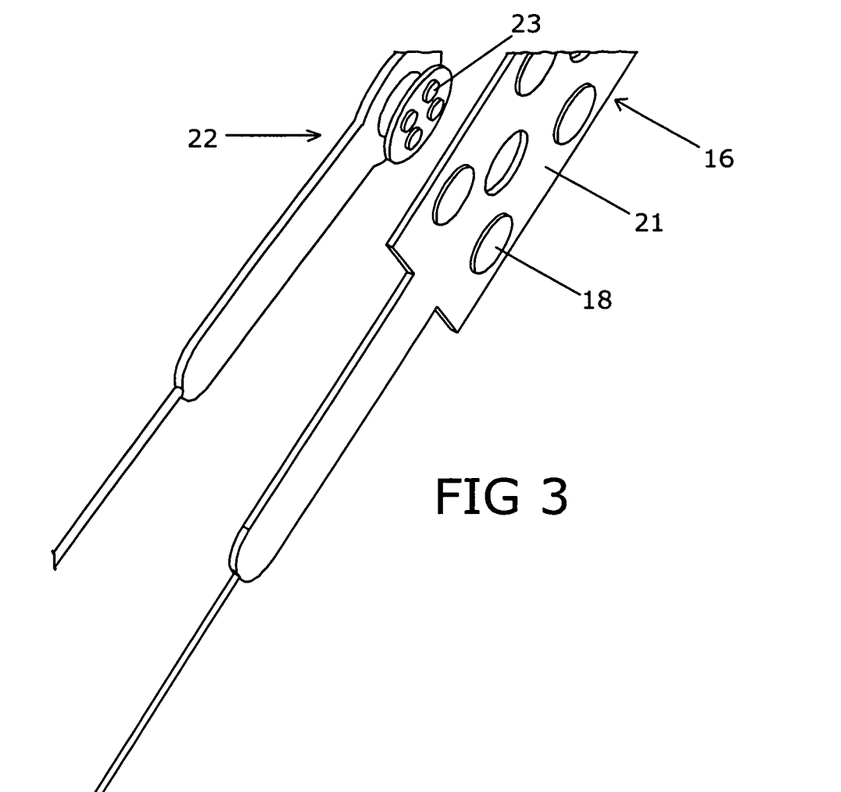
FIG. 3 is a perspective view showing another electrode structure positioned for placement into a thru hole of a cortical strip or grid electrode structure.
Figure 4:
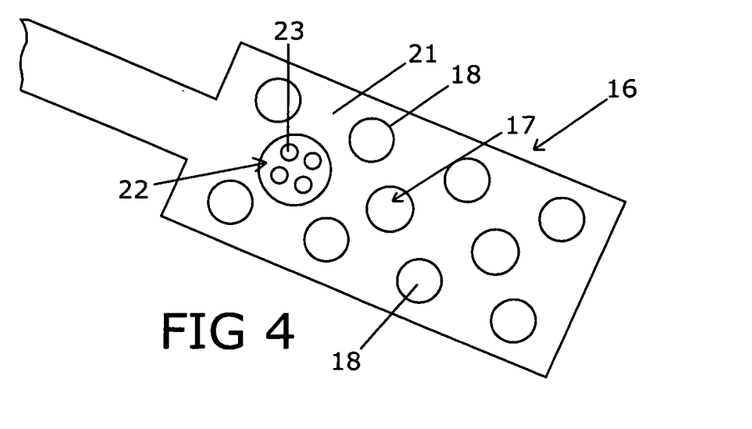
FIG. 4 is a plan view showing the electrode structure of FIG. 3 positioned into the thru hole of the cortical strip or grid electrode structure.
Figure 5:
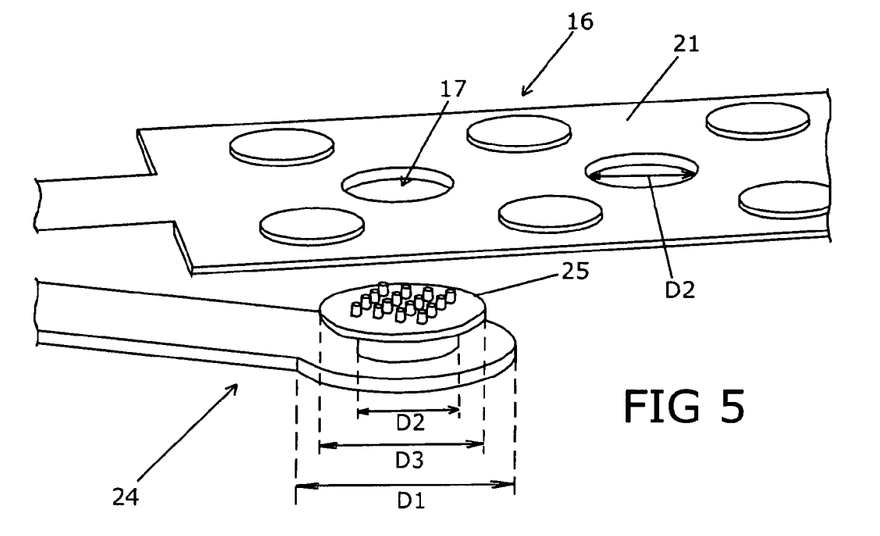
FIG. 5 is a perspective view showing another micro-wire electrode structure positioned for placement into a thru hole of a cortical strip or grid electrode structure.
Figure 6:
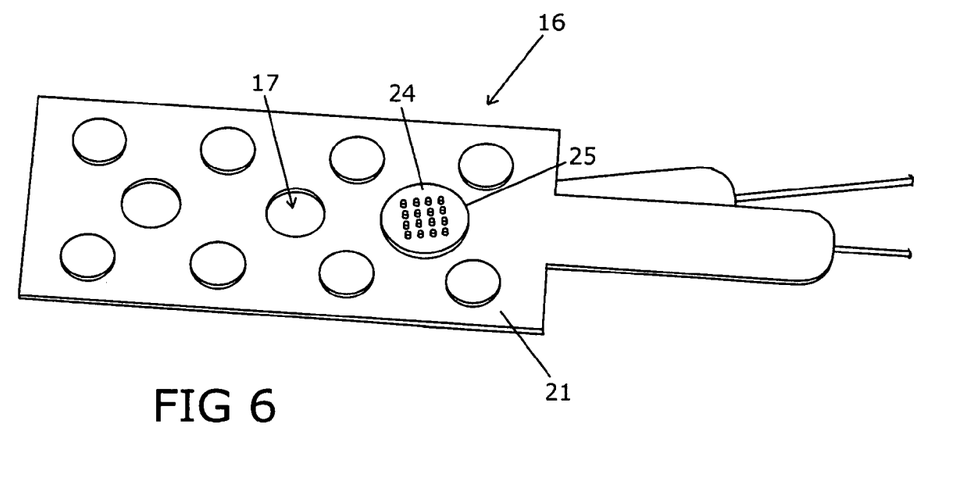
FIG. 6 is a bottom plan view showing the micro-wire electrode structure of FIG. 5 mounted in the thru hole of the cortical strip or grid electrode structure.
Figure 7:
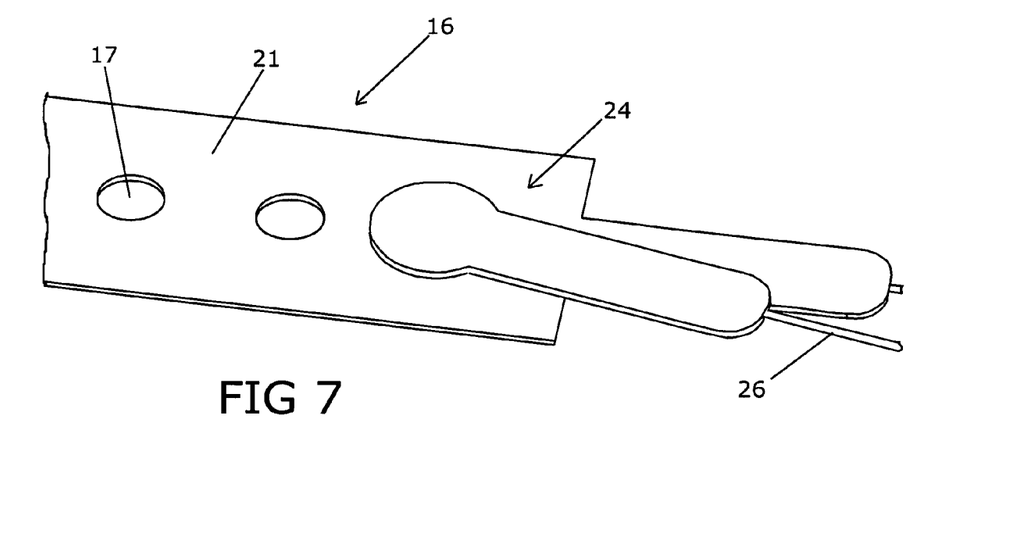
FIG. 7 is a top view of a micro-wire electrode structure and cortical strip electrode assembly.

In FIG. 1, the second electrode structure 10 is shown to have a single macro electrode contact 19 and a micro-wire electrode array 12, in FIG. 2, macro electrode contact 19 is shown, in FIGS. 3 and 4 a pattern of macro electrode contacts 23 is shown and in FIGS. 5-7 a micro-wire electrode array 25 is shown. As further discussed below with respect to FIGS. 17 and 18, depth electrode structures may also be utilized in conjunction with a base cortical electrode device. Accordingly, the second electrode structure may add a variety of electrode contacts and micro-wire electrode arrays to form a cortical electrode assembly according to the teachings of the present invention.

The cortical electrode strips and grids of the present invention are manufactured with thru-holes in a Silastic® silicone substrate which allow for a micro-wire or depth electrode structure, for example, to be routed through selected thru-holes. Silastic® is a trademark of Dow Corning Corporation for flexible inert silicone elastomers which because its inert nature, medical grade Silastic silicone elastomers or similar elastomers are preferred in the structure of the present invention. The cortical strips and electrode grids are manufactured and provided with thru-holes in the Silastic® silicone substrate which are used to attach the micro-wire electrode array or other second electrode structures to the base cortical electrode bodies.

Figure 8:
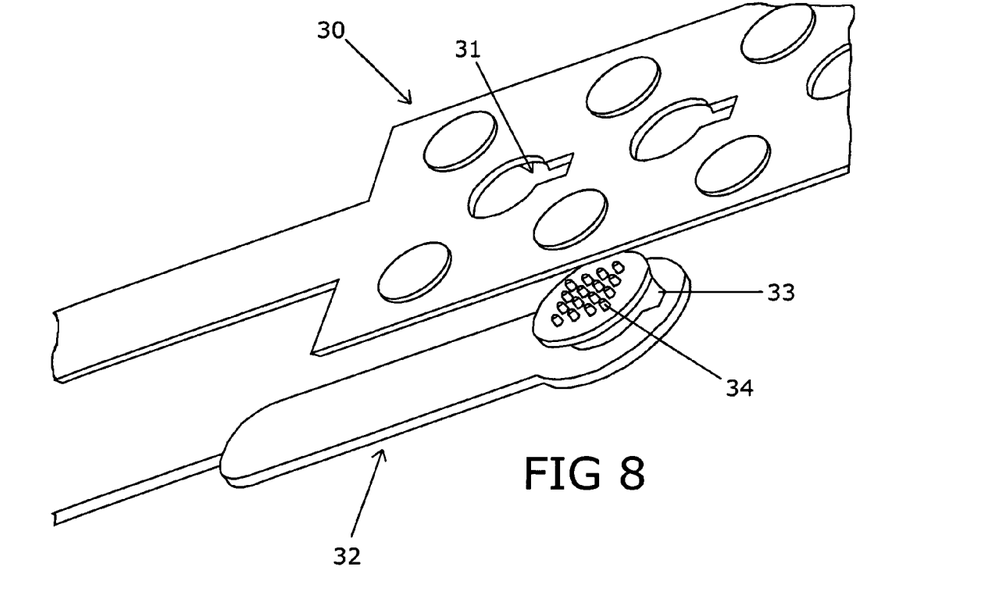
FIG. 8 is a perspective view showing a slotted micro-wire electrode structure positioned for placement in a slotted thru hole of a cortical strip or grid electrode structure.
Figure 9:
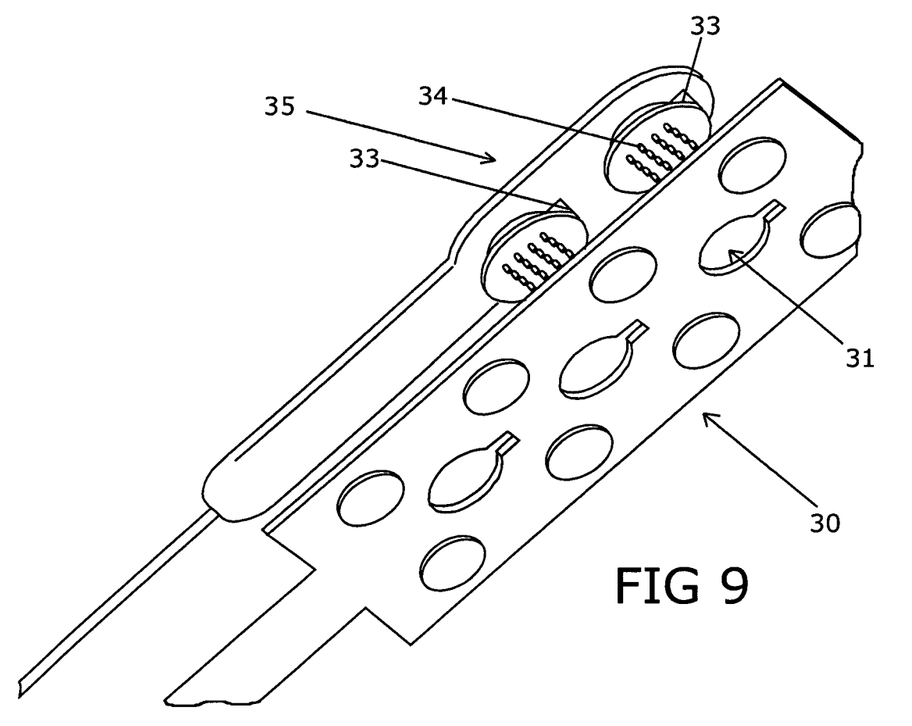
FIG. 9 is a perspective view showing a double slotted micro-wire electrode structure positioned for placement in the slotted thru holes of a cortical strip or grid electrode structure.
Figure 10:
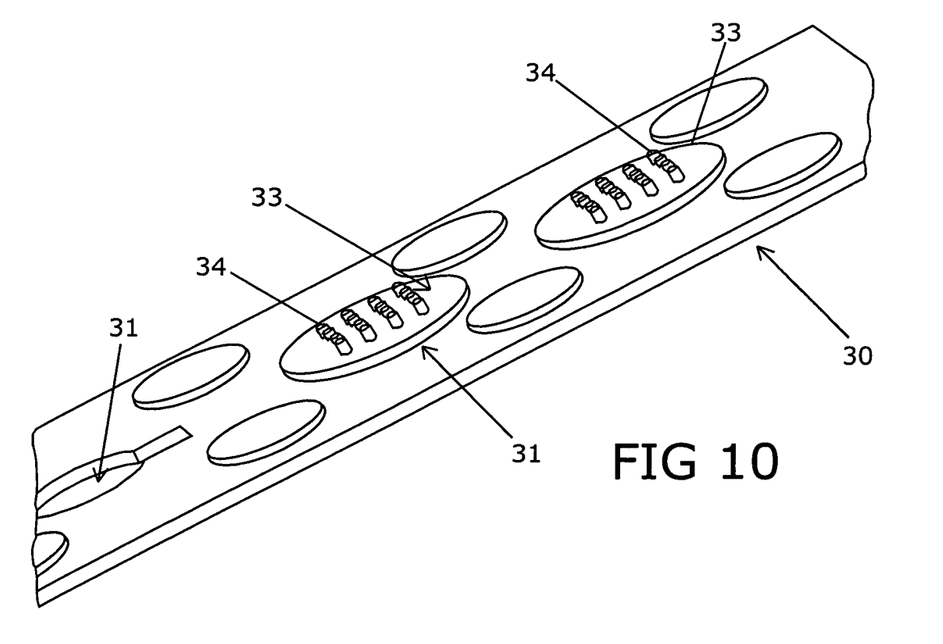
FIG. 10 is a perspective view showing the micro-wire structure of FIG. 9 mounted in the cortical electrode structure.

FIGS. 8-10 show another embodiment of the invention. Cortical strip or grid electrode structure 30 is shown having keyhole-shaped thru-holes 31 which cooperate with micro-wire electrode structures 32 and 35. The second electrode structure 32 is shown having body extension 33 with a micro-wire electrode array 34 in FIG. 8. In FIGS. 9 and 10 the micro-wire electrode device 35 is shown having a pair of micro-wire electrode arrays 34 protruding from keyhole-shaped electrode bodies 33. The keyhole apertures provide for a secure positioning of the second electrode structure.

As discussed with respect to FIGS. 1 and 2, the micro-wire electrode structures 10 and 20 have essentially three-part end structures comprised of generally circular portions with diameters 13, 14 and 15, respectively. The mid portion essentially forms a peripheral channel which fits within thru holes 17 of the cortical strip grid electrode body 21.

The micro-wire substrate end shape is generally that of a "grommet" like structure having, for example, three diameters ($D_1$, $D_2$, $D_3$ or 13, 14, 15) of silicone substrate stacked on top of one another where the middle diameter ($D_2$) is the smallest diameter, typically approximately 0.1875 inches or 4.76 mm. The small diameter center section ($D_2$) generally has the same or similar diameter of a thru-hole 17 which may be punched into the silicone flat sheet substrate of a standard cortical strip or grid electrode structure.

The three diameters ($D_1$, $D_2$, $D_3$) of the micro-wire array structure end are constructed and arranged so that the electrode array may be securely fastened to the cortical grid or strip electrode in a similar way that a grommet functions when mated with a flat component having a thru hole.

Manufacturing Process

Figure 11:
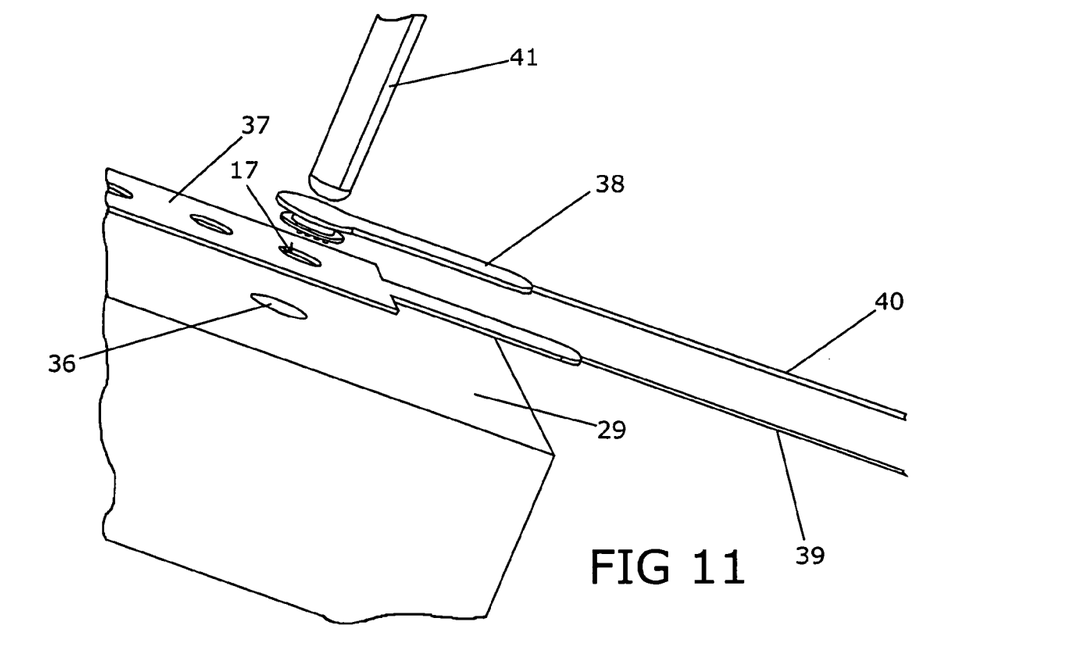
FIG. 11 is a perspective view showing an introducing rod above a micro-wire electrode structure positioned for placement into the thru hole of a cortical strip electrode structure and aligned with the aperture of the assembly platform.
Figure 12:
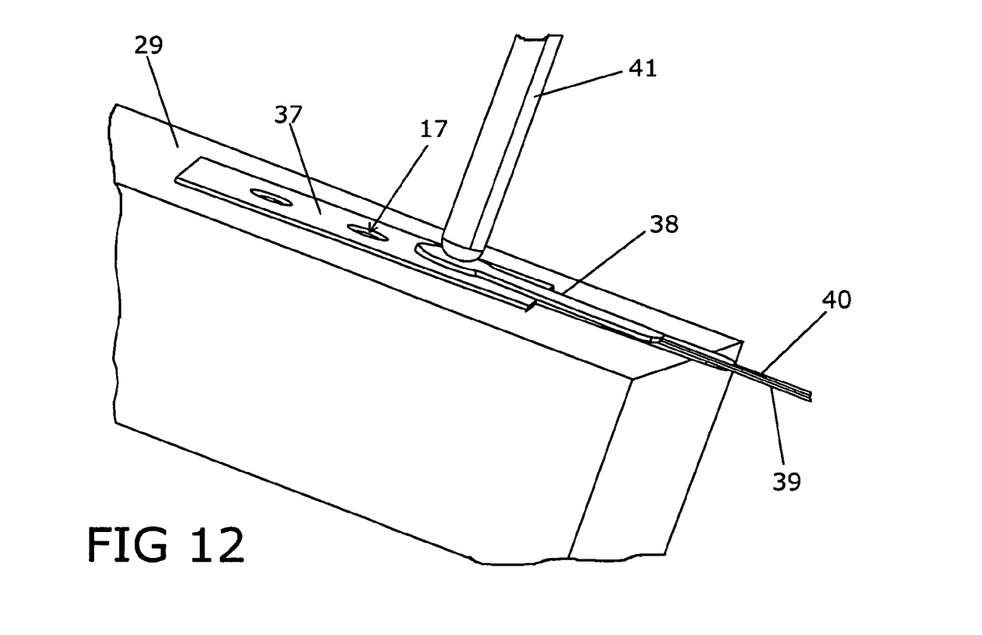
FIG. 12 is a perspective view showing the introducing rod having pushed the micro-wire electrode into the thru hole of the cortical strip electrode structure as shown in FIG. 11.

In the process of the present invention, the micro-wire electrode array structures are joined to a cooperating cortical grid or strip electrode structure. Referring to FIGS. 11 and 12, to attach the micro-wire electrode array of the electrode structure 38 to a cortical grid or strip electrode structure 37, the following steps are performed:

First, it is determined which thru hole 17 on the grid/strip electrode structure 37 the micro-wire array structure 38 should be mated and next the hole 17 is aligned so it is concentric with the hole 36 in the assembly platform 29. The electrode contacts should be facing downward. Next, with the micro-wires facing downward, the micro-wire electrode array structure 38 is set so that the substrate is concentric with the hole 17 in which it is to be mounted so that the lead 40 of the electrode array 38 is running generally parallel with the leads 39 of the grid/strip structure 37. Next, a handheld introducing rod 41 is grasped to press the center of the micro-wire array 38 lightly downward until the first diameter section (i.e., 15) of the electrode array body fully passes through the smaller hole 17 of the grid/strip structure. This attachment method is preferably conducted in a sterile operating field because gloves that medical professionals wear makes finessing the micro-wire array's intricate features into a hole smaller than the micro-wire array's bottom surface challenging. The thru-holes punched through the strip/grid are not only used for attaching micro-wire arrays, but as discussed below may also be used for passing through depth electrode structures in the cases where a strip/grid electrode structure is placed along a line where a depth electrode is to be located.

Figure 13:
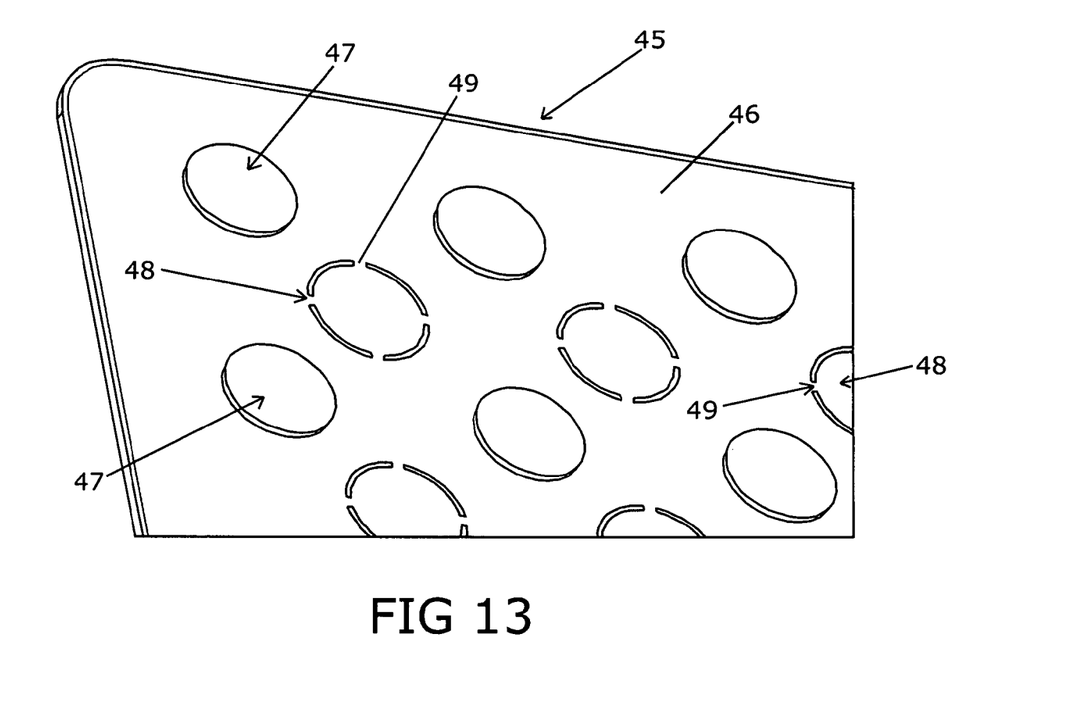
FIG. 13 is a perspective view showing pre-perforated holes positioned in the electrode grid substrate of an electrode structure.

Referring to FIG. 13, holes 48 are shown pre-perforated in such a way that silicone 49 remains attached to the silicone grid substrate 46. For example, the silicone from the pre-perforated holes 48 is shown attached in four locations 49 at generally 90 degrees separating the silicone that is not punched out. This arrangement may be modified by a different form of pre-punched holes 48 positioned around the perimeter of the hole. Additionally, these pre-perforated holes may have a radiopaque or similar type of marker that would show up during Magnetic Resonance Imaging (MRI), x-rays or CAT scans. This allows a medical technician to keep track of what silicone circles are removed from the grid during scanning.

Figure 14:
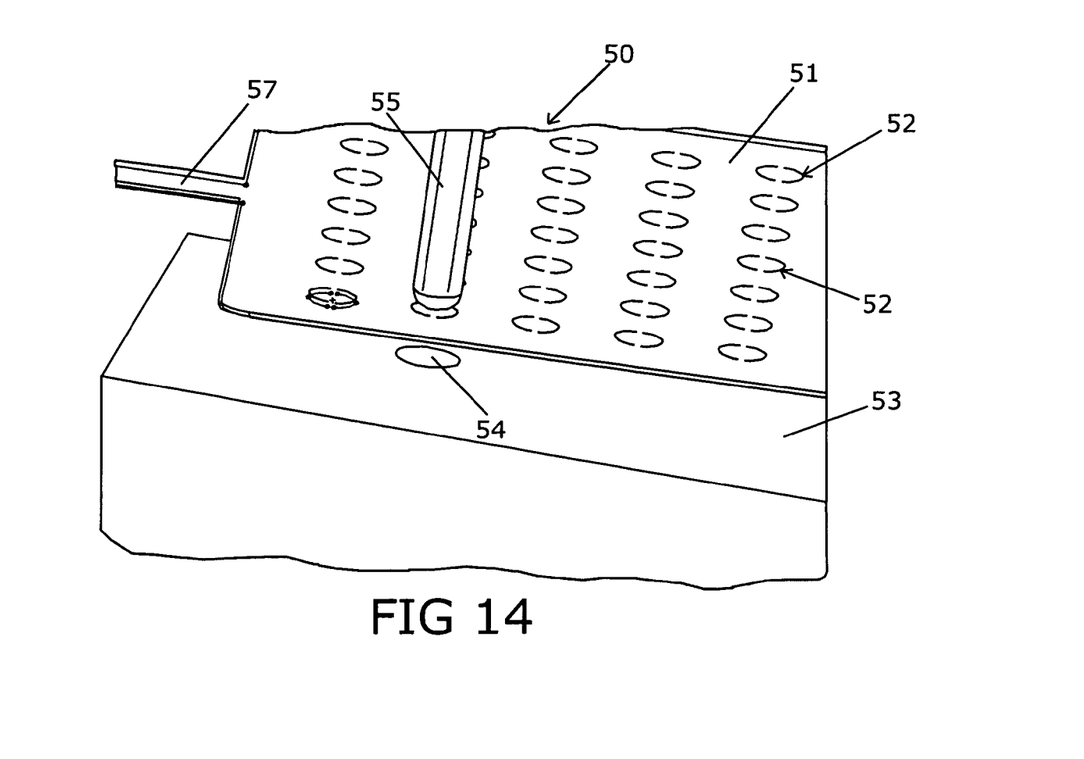
FIG. 14 is a perspective view showing a guiding stylet aligned with a perforated hole positioned above an aperture in an assembly block.

FIG. 14 shows a hole being created from a perforated hole or aperture 52. A neurosurgeon or nurse, for example, may place the perforated hole concentrically with a block 53 having a hole 54 with approximately the same diameter as that of a perforated hole 52. A guiding stylet 55 may then be pressed down concentrically on the perforated hole to remove the silicone circle, for example, thus creating a through hole in the body 51 of the silicone substrate electrode grid 50.

Figure 15:
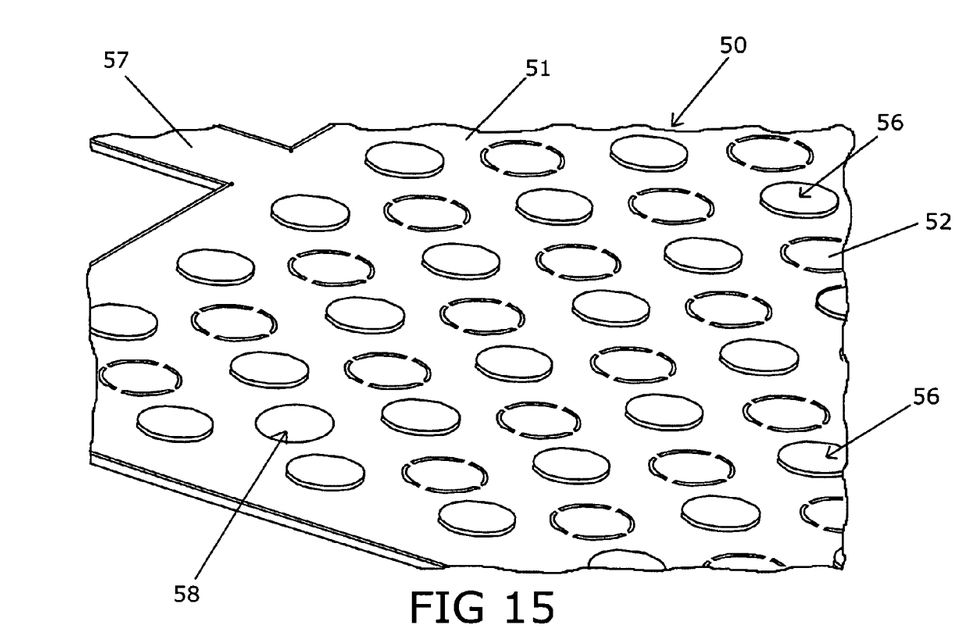
FIG. 15 is a perspective view showing the electrode grid structure having a perforated hole removed.
Figure 16:
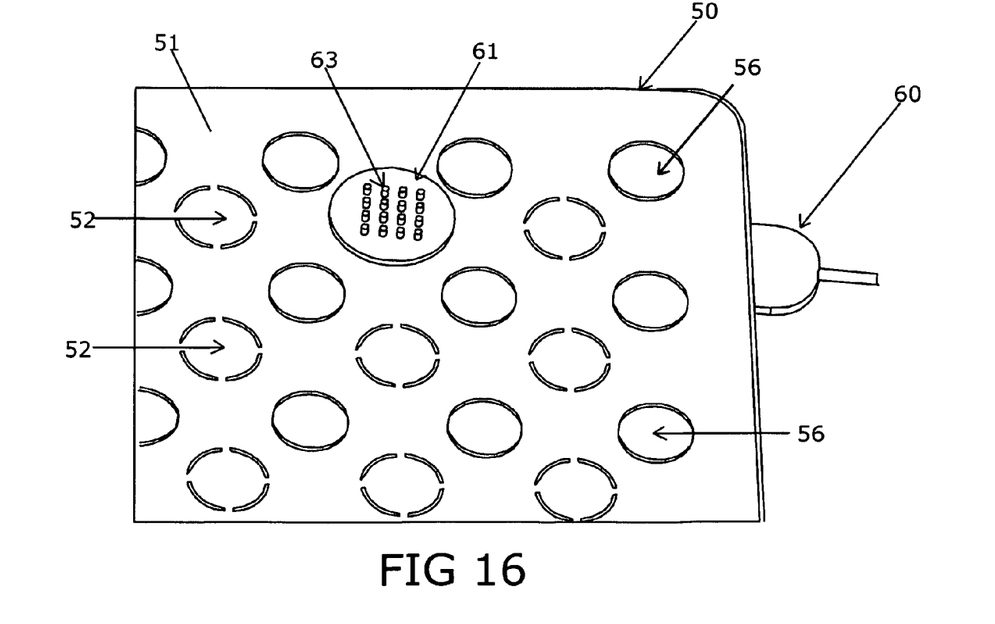
FIG. 16 is a perspective view showing a micro-wire electrode inserted into an aperture of the electrode grid.

FIGS. 15-16 show another electrode configuration requiring only specific holes for insertion of a micro-wire insert (FIG. 16). It is preferable to leave the remaining perforated holes 52 filled with silicone to prevent movement of the brain and skull dura from growing through open holes.

Figure 17:
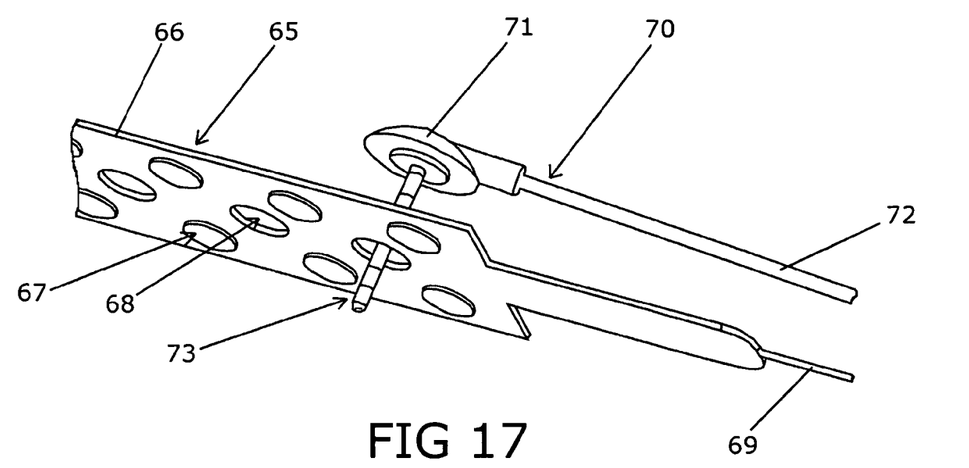
FIG. 17 is a perspective view showing a depth electrode structure being positioned into a thru hole of an electrode structure.
Figure 18:
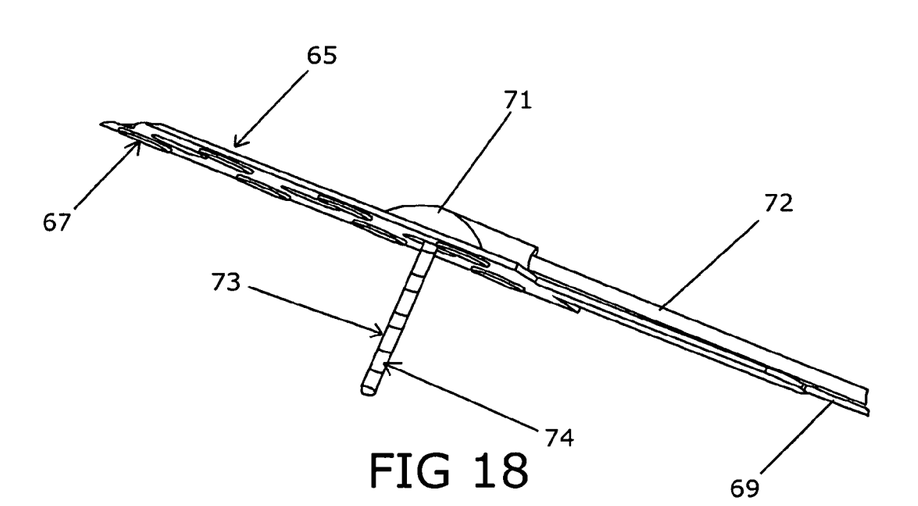
FIG. 18 is a perspective showing the depth electrode structure of FIG. 17 mounted into the electrode grid structure.

Referring to FIGS. 17-18, a depth electrode structure 70 is shown having a guiding feature that fits concentrically in the through holes 68 of the electrode 65 and is shown being positioned in a hole 68 of the substrate grid of the electrode structure 65. The depth electrode structure 70 is shown having electrode head 71, lead wire 72, electrode contacts 73 with electrodes 74 and is configured for use inside the brain. Electrode 65 is shown having electrode body 66, electrode contacts 67, holes or apertures 68 and lead wire 69.

In summary, the present invention provides micro-wire electrode array body structures having multiple diameters where the outside diameters are used as fixation surfaces and where one specified diameter allows the electrode device to mate with a similar sized thru-hole in a grid of a base electrode structure. The micro-wire electrode array may have different sized micro-wires, i.e., different diameter micro-wire contacts, and may also include macro contact discs. Macro-contact arrays (single or multiple macro contact discs) may also be utilized. The micro-wire array of the second electrode may mate with multiple thru holes in different areas of the electrode grid of the first or base electrode structure. The thru hole and mating configuration of the second micro-wire electrode array may also have a keyed or like configuration that only allows for the placement in one direction of the second electrode with respect to the cortical strip electrode to prevent rotation of the micro-wire array device in the thru-hole of the base cortical strip electrode. The assembly components are steam autoclavable stainless steel or platinum alloy or the like. Further, a process for forming multi-part electrode assemblies is described.

As many changes are possible to the cortical electrode assemblies and process of forming electrode assemblies of this invention utilizing the teachings thereof, the descriptions above and the accompanying drawings should be interpreted in the illustrative and not in the limited sense.

That which is claimed is:

1. A cortical electrode assembly having selectable electrode sites comprising:
   a) a first flexible electrode body having a planar configuration with an upper surface and a lower surface, said lower surface having a plurality of electrode contacts, said first electrode body further having a plurality of thru-holes; and
   b) a second electrode body having a grommet-like structure with at least one electrode contact, said grommet-like structure having a radial channel for fixing said second electrode body in a selected thru-hole of said first electrode body, whereby upon placement of said second electrode body in a selected thru-hole provides addition of said at least one electrode contact of said second electrode body to said plurality of electrode contacts of said first electrode body and for said cortical electrode assembly.

2. The cortical electrode assembly of claim 1, wherein said plurality of thru-holes are defined by perforations through said first flexible electrode body and whereby said selected thru-hole is formed upon removal of a perforated thru-hole area.

3. The cortical electrode assembly of claim 1, wherein said plurality of electrode contacts of said first electrode are in a grid pattern and wherein said plurality of thru-holes of said first electrode body are circular and interspersed within said grid pattern.

4. The cortical electrode assembly of claim 1, wherein said second electrode body has an electrode contact selected from the group of electrode contacts consisting of a macro electrode contact, a micro electrode contact, a depth electrode and a combination of a macro electrode contact and a micro electrode contact.

5. The cortical electrode assembly of claim 1, wherein said thru-holes in said first flexible electrode body have a keyhole configuration.

6. The cortical electrode assembly of claim 1, wherein said first and second electrode bodies are formed of medical grade silicone.

7. The cortical electrode assembly of claim 2, wherein each said perforated thru-hole has a radiopaque marking for detection.

8. A cortical electrode assembly having selectable electrode contact sites comprising a first flexible electrode body having a planar configuration having a plurality of electrode contacts in a predetermined pattern and a plurality of thru-holes each having a predetermined configuration and being interspersed within said predetermined pattern of said plurality of electrode contacts, said plurality of thru-holes adapted for receiving a second electrode body having an outwardly extending grommet-like body with an electrode contact, the outwardly extending grommet-like body having a peripheral channel for fixing the second electrode body in a selected thru-hole of said first flexible electrode body by means of the peripheral channel of the grommet-like body.

9. The cortical electrode assembly of claim 8, wherein said plurality of thru-holes are defined by perforated areas and adapted for selective removal from said first flexible electrode body.

10. The cortical electrode assembly of claim 8, wherein said assembly further comprises a second electrode body having an outwardly extending grommet-like body with an electrode contact, said outwardly extending grommet-like body having a peripheral channel.

11. The cortical electrode assembly of claim 10, wherein said second electrode body has an electrode contact selected from the group of electrode contacts consisting of a macro electrode contact, a micro electrode contact, a depth electrode and a combination of a macro electrode contact and a micro electrode contact.

12. The cortical electrode assembly of claim 9, wherein said perforated areas are marked with a radiopaque marking.

13. The cortical electrode assembly of claim 10, wherein said first flexible electrode body is of a silicone composition and wherein said second flexible electrode body is formed of a silicone composition.

14. A two part cortical electrode assembly having selectable electrode sites comprising:
   a) a first flexible electrode body structure having a planar surface and a plurality of electrode contacts arranged in a predetermined pattern, said first flexible electrode body further having a plurality of thru-holes arranged across said planar surface and within confines of said electrode pattern of said first electrode body structure;
   b) a second electrode body structure having an outwardly extending surface with at least one electrode contact for extension through a selected thru-hole of said first electrode body structure; and
   c) wherein said second electrode body has a grommet-like structure with a peripheral channel.

15. The two part cortical electrode assembly of claim 14, wherein said thru-holes are perforated structures and adapted to form said thru-holes through said first electrode body upon the selected removal of the perforated structure.

16. The two part cortical electrode assembly of claim 14, wherein said means to fix said second electrode body in said selected thru-hole of said first flexible electrode body structure is a frictional fit.

17. The two part cortical electrode assembly of claim 16, wherein said second electrode body includes an electrode contact selected from the group of electrode contacts consisting of a macro electrode contact, a micro electrode contact, a depth electrode and a combination of a macro electrode contact and a micro electrode contact.

18. The two part cortical electrode assembly of claim 14, wherein said grommet-like structure is for positioning of said channel about said selected thru-hole periphery.

19. The two part cortical electrode assembly of claim 15, wherein each said perforated thru-hole has a radiopaque marking for detection.

20. The two part cortical electrode assembly of claim 14, wherein said first and second electrode bodies are formed of medical grade silicone.

\* \* \* \* \*